United States Patent [19]
Wright

[11] Patent Number: 5,415,616
[45] Date of Patent: May 16, 1995

[54] ROTOR-PROTECTED EVACUATION PORT FOR CENTRIFUGAL SEPARATION

[75] Inventor: Herschel E. Wright, Gilroy, Calif.

[73] Assignee: Beckman Instruments, Inc., Fullerton, Calif.

[21] Appl. No.: 271,856

[22] Filed: Jul. 7, 1994

[51] Int. Cl.⁶ ............... B04B 5/02; B04B 15/08
[52] U.S. Cl. ........................... 494/16; 494/61
[58] Field of Search ............... 494/10, 12, 13, 14, 494/16, 25, 35, 39, 42, 60, 61; 210/406, 416.1; 436/45; 422/72

[56] References Cited

U.S. PATENT DOCUMENTS

| | | | |
|---|---|---|---|
| 2,670,898 | 3/1954 | Pickels | 494/61 X |
| 3,246,688 | 4/1966 | Colburn | 494/10 X |
| 3,300,129 | 1/1967 | Brunati | 494/10 X |
| 3,604,617 | 9/1971 | Patterson | 494/61 X |
| 4,011,972 | 3/1977 | Pederson et al. | |
| 4,193,536 | 3/1980 | Kubota | |
| 4,223,829 | 9/1980 | Bange | |
| 4,435,169 | 3/1984 | Romanauskas | 494/20 |
| 4,857,811 | 8/1989 | Barrett et al. | 318/3 |
| 5,084,133 | 1/1992 | Guy et al. | 159/47.1 |

FOREIGN PATENT DOCUMENTS

3630483  6/1987  Germany ............... 494/16

Primary Examiner—David A. Scherbel
Assistant Examiner—Charles Cooley
Attorney, Agent, or Firm—William H. May; Gary T. Hampson; Schneck & McHugh

[57] ABSTRACT

A device for centrifugally separating a sample includes a housing which defines an enclosed chamber from which gas is evacuated via an evacuation port protected by a spinning rotor. The evacuation port is preferably located proximate to the axis of rotation of the rotor and within the interior of the rotor. A drive shaft connects the rotor to a motor positioned outside of the chamber. An annular sleeve having an inside diameter greater than the diameter of the shaft extends coaxially along the drive shaft into the chamber. The outlet of the gap between the drive shaft and the annular sleeve defines the evacuation port. A hub is fixed to the upper end of the drive shaft and includes a downwardly depending skirt that has an inside diameter greater than the outside diameter of the annular sleeve. Gas evacuation from the chamber is initially in an upward direction along the gap between the hub skirt and the sleeve and in a downward direction from the evacuation port to a vacuum pump. Preferably, the vacuum pump is also joined to the drive motor.

17 Claims, 1 Drawing Sheet

ROTOR-PROTECTED EVACUATION PORT FOR CENTRIFUGAL SEPARATION

TECHNICAL FIELD

The present invention relates generally to centrifuges and more particularly to evacuating gas from a centrifuge.

BACKGROUND ART

Centrifugation of a biological or chemical sample in order to separate sample components requires high angular velocities. A drive system of a centrifuge may be required to spin a sample-containing rotor at 100,000 revolutions per minute. Air friction along the surface of the rotor is one factor that limits the maximum speed that can be achieved using a given drive motor. This friction is referred to as "windage." Windage not only acts as a limiting factor to the maximum angular velocity of a rotor, but also generates thermal energy that potentially increases the temperature of the sample to be centrifugally separated.

To counteract the effect of windage on the temperature of the sample, centrifuge instruments may include a refrigeration system. For example, refrigeration coils may be placed in surface contact with the exterior of a chamber of a centrifuge.

The effects of windage on rotor speed and temperature can be reduced by at least partially evacuating the centrifuge chamber. A vacuum pump may be connected to the chamber to achieve atmospheric conditions that reduce windage. However, the connection of the vacuum pump may significantly influence the cost of the centrifugal instrument. Typically, the chamber includes a removable cover. One option is to connect the vacuum pump to the cover. As compared to attachment to a fixed structure, attachment to the movable cover requires an increase in the length of interconnect hoses and requires the use of vacuum seals that are able to withstand the periodic stresses caused by pressure differential on the cover.

Another concern in the attachment of a vacuum pump to a centrifuge housing is minimizing the risk of foreign matter entering the vacuum pump. Even with careful handling, a sample may spill into the enclosed chamber defined by the centrifuge housing. If the material enters the vacuum pump, the efficiency of the pump may be adversely affected. Moreover, the useful life of the pump may be reduced. U.S. Pat. No. 4,857,811 to Barrett et al. describes the use of a vacuum pump having an inlet at a bottom surface of an enclosed chamber. While this position of the inlet is cost-efficient, the position is one in which gravitational forces will cause spillage and other foreign matter to enter into the pump. Alternatively, the inlet may be at sidewalls of the chamber. However, with the rotation of the rotor, a sample may be thrown directly from the rotor to the inlet, or may indirectly reach the inlet by first striking a sidewall and then being forced to the inlet by vacuum forces and the swirl created by the rotating rotor.

U.S. Pat. No. 5,084,133 to Guy et al. teaches a centrifuge of the type referred to as an evaporator-concentrator. A small quantity of gas is temporarily and periodically admitted into the vessel. The admitted gas is heated by a resistor for the purposes of heating the specimens to be concentrated and accelerating the rate of evaporation. A vacuum pump is connected to a chamber by a path through a rotating hub. Because the orifice to the path through the rotor is directed upwardly to the heating resistor, the structure is susceptible to the entrance of spilled sample or other foreign matter into the vacuum system.

An object of the present invention is to provide a device for centrifugally separating a sample, wherein a chamber may be evacuated in a manner that does not render a vacuum system susceptible to the entrance of foreign matter.

SUMMARY OF THE INVENTION

The above object has been met by a centrifugal device in which an evacuation port is positioned away from walls of the device and is protected by a rotor. In the preferred embodiment, a gas evacuation path follows a drive shaft for rotating the rotor. The evacuation port is within the interior of the rotor. Gas flow from an enclosed chamber in which the rotor is housed is upward to the evacuation port within the interior of the rotor and then downward along the drive shaft. Because the path from the enclosed chamber to the evacuation port is in an upward direction, the likelihood that foreign matter will be fed into the vacuum system is minimized. Moreover, high speed rotation of the rotor generates forces that are contrary to any forces that would cause foreign matter to follow the evacuation of gas from the enclosed chamber.

A drive motor is connected to the drive shaft at an end of the shaft that is outside of the enclosed chamber. In one embodiment, a sleeve extends coaxially along the drive shaft in spaced relationship with the drive shaft. A vacuum pump is in fluid communication with the gap between the sleeve and the drive shaft. The evacuation port is an annular opening between the drive shaft and the sleeve at the upper end of the sleeve.

A hub having a downwardly depending skirt is fixed to the upper end of the drive shaft. The inside diameter of the skirt is greater than the outside diameter of the sleeve, leaving an annular path for the evacuation of gas from the enclosed chamber to the evacuation port. Thus, an upward path to the evacuation port has a side-by-side relationship with a downwardly directed path from the evacuation port to a vacuum pump.

Any of a variety of rotors may be attached to the hub. Attachment may be by any of the conventional techniques. For example, the hub may have an internally threaded bore to receive a bolt that extends through the rotor for affixing the rotor to the hub.

While not critical, the invention preferably includes a path from the drive motor to the vacuum pump. The sleeve may extend to the drive motor to allow fluid communication between the vacuum pump and the drive motor.

An advantage of the present invention is that the inverted U-shaped path for the evacuation of gas from the enclosed chamber effectively prevents gravity feed of spillage and other foreign matter into the evacuation port. Therefore, the susceptibility of a vacuum system to ingesting foreign materials is reduced. The susceptibility is further reduced by forming the vacuum path close to the axis of rotation of the rotor. In this design, material must move against the radial flow of the spinning rotor in order to enter the vacuum system. Consequently, the effectiveness of the vacuum pump is preserved. Another advantage is that the penetration of the evacuation path into the enclosed chamber along the drive shaft frees the bottom wall of the housing for attachment of refrigeration coils to be used in temperature control of a centrifugal separation. Thus, any or all of the sidewalls, bottom walls and cover may be provided with refrigeration coils.

BEST MODE FOR CARRYING OUT THE INVENTION

Figure 1:
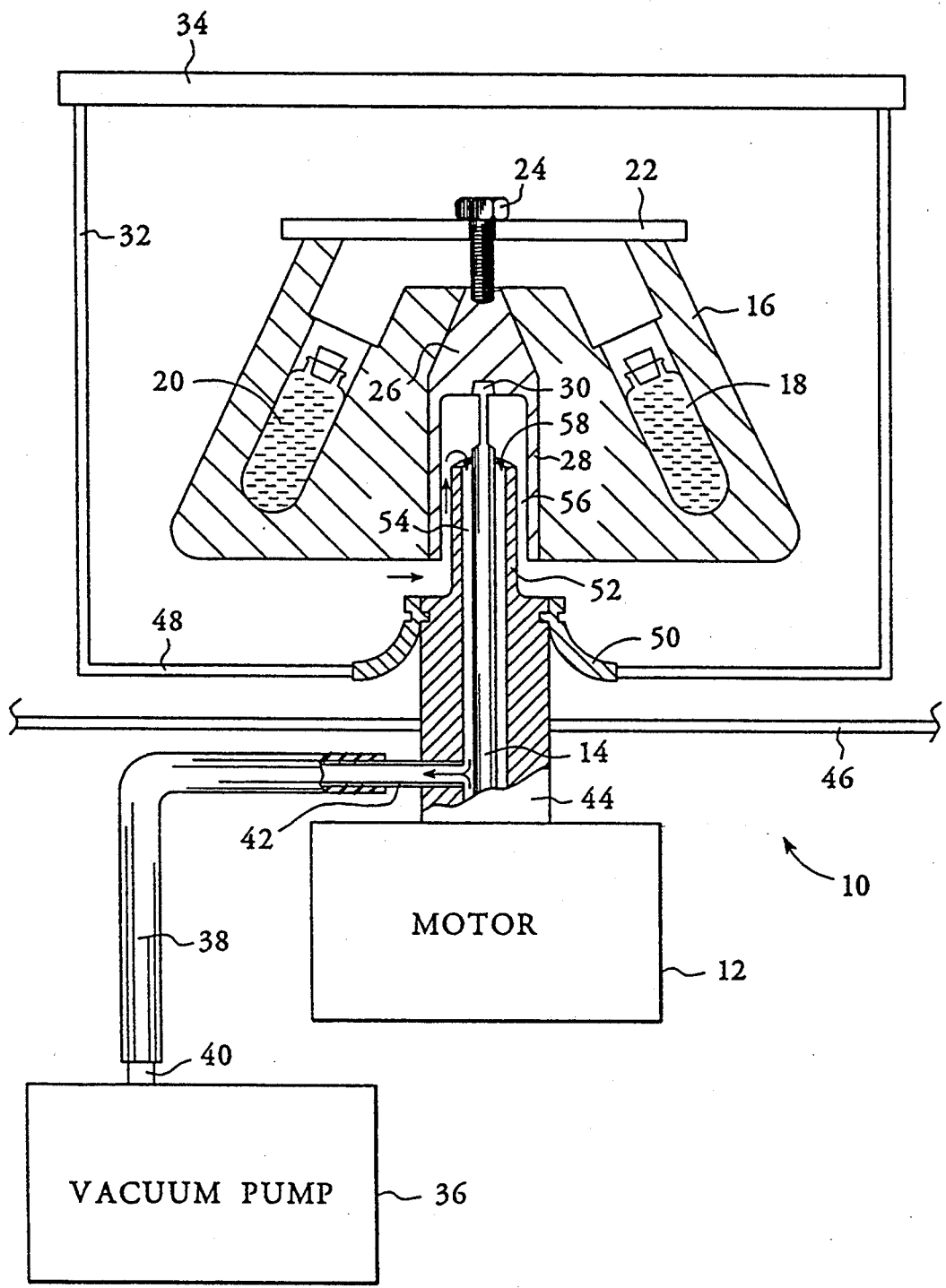
FIG. 1 is a side sectional view of a centrifuge having a vacuum system in accordance with the present invention.

With reference to FIG. 1, a centrifuge 10 includes a drive motor 12 for rotating a drive shaft 14. While not critical, the drive motor may be an AC inductive polyphase motor. The induction motor may be of the type to drive a rotor 16 at a rate as great as 100,000 revolutions per minute.

The rotor 16 is shown as having compartments for securing at least two specimen containers 18 and 20 for the centrifugal separation of components. The containers 18 and 20 are placed in the rotor 16 by removing a rotor lid 22. A bolt 24 extends through a hole in the rotor lid and is received within an internally threaded bore of a hub 26. The bolt secures the rotor lid 22 to the rotor 16 and secures the rotor to the hub 26.

The hub 26 has a cylindrical, downwardly depending skirt 28. The hub is fixed to the upper end of the drive shaft 14 such that the cylindrical skirt is coaxial to the drive shaft 14. The rotational drive of the induction motor 12 is transferred to the rotor 16 by means of the drive shaft 14 and the hub 26. The upper end 30 of the drive shaft may be secured to the hub using conventional techniques. The rotor 16 has an internal surface configured to receive the hub 26. Any of a variety of types of rotors may be connected to the hub.

The rotor 16, the hub 26 and the upper portion of the drive shaft 14 are contained within a chamber defined by a housing 32 having a cover 34. While not shown, typically vacuum seals are located at the interface of the cover with the remainder of the housing. The sidewalls and the bottom wall of the housing 32 may be a metallic framework having refrigeration coils at exterior surfaces to control the temperature within the enclosed chamber defined by the housing.

In addition to temperature control, the atmosphere within the enclosed chamber of the housing 32 may be controlled by operation of a vacuum pump 36. A conduit 38 is connected to a fitting 40 that extends from the vacuum pump. At the opposite end of the conduit, the conduit is friction fit to a fitting 42 of a sleeve 44. The sleeve 44 has a lower, large diameter portion that extends coaxially with the drive shaft 14 to penetrate openings in an outer framework 46 and the bottom wall 48 of the housing 32. A vacuum seal 50 connects the bottom wall to the sleeve 44 to prevent leakage of air into the enclosed chamber of housing 32 after the evacuation of air from the housing.

A reduced diameter portion 52 of the sleeve 44 extends into the downwardly depending skirt 28 of the hub 26. The inside diameter of the sleeve is greater than the outside diameter of the drive shaft 14. Thus, a first annular gap 54 is formed between the drive shaft and the inner surface of the sleeve. In turn, the outside diameter of the sleeve at the portion 52 that extends into the hub skirt 28 is less than the inside diameter of the skirt, providing a second annular gap 56. Merely for example, the diameter of the drive shaft may be approximately 8 mm, while the inside diameter of the skirt 28 may be 22 mm. An acceptable thickness of the portion 52 is slightly less than 3 mm.

The upper extent of the sleeve 44 is spaced apart from the hub 26. The region of the first annular gap 54 surrounded by the upper extent of the portion 52 of the sleeve 44 is referred to herein as the "evacuation port 58." However, other embodiments of evacuation ports are contemplated. For example, one or more bores can be formed along the circumference of a sleeve that is sealed at its upper end. Gas flow from the enclosed chamber of the housing 32 to the vacuum pump 36 is upward with approach to the evacuation port 58 and is downward with departure from the evacuation port 58. Arrows are provided in FIG. 1 to illustrate the direction of the flow of air.

The sleeve 44 extends downwardly in spaced relationship with the drive shaft 14 to the drive motor 12. Thus, the vacuum pump 36 removes air from the motor assembly as well as the chamber of the housing 32.

In operation, the rotor 16 is driven at a high rate of speed by the drive motor 12. The maximum angular velocity of the rotor will be limited by a number of factors. One of these factors is the fluid friction of the rotor against air, sometimes referred to as "windage." The vacuum pump 36 at least partially evacuates air from the enclosure, thereby limiting the effects of windage. Providing a vacuum pressure of 100 millitorr is contemplated.

One concern in the evacuation of air from the housing 32 involves preventing foreign matter from entering the vacuum pump 36. For example, if an evacuation port were to be located at the bottom wall 48 of the enclosure 32, any spillage of sample from one of the containers 18 and 20 could readily drain into the evacuation port. However, in the structure of FIG. 1, the evacuation port 58 into the sleeve 44 is surrounded by the downwardly depending skirt 28 of the hub 26. Because access to the evacuation port 58 requires upward passage through the second annular gap 56, foreign matter will not be gravitationally fed into the evacuation port.

The rotor 16 has an angular velocity that further acts to prevent the passage of foreign material into the vacuum pump 36. To enter the pump, material on the walls of the housing 32 would be required to move toward the center of the chamber. Such movement would be in the direction against the radial flow caused by the spinning rotor. In this manner, operation of the rotor protects the evacuation port 58 from the entrance of material which could threaten the motor 12 and the vacuum pump 36.

As an alternative to the embodiment of FIG. 1, the downwardly depending skirt 28 of the hub 26 could extend beyond the lower surface of the rotor 16, and the sleeve 44 could extend into the skirt but not reach the interior of the rotor. This embodiment would still require upward movement of material to reach the evacuation port 58 defined at the end of the sleeve. The embodiment would also require movement of matter against the force generated by the spinning rotor. However, in this embodiment, the rotor would be somewhat less protective.

The invention claimed is:

1. A device for centrifugally separating a sample retained by a rotor having walls that define an axial cavity to receive a rotary drive mechanism, said device comprising:

a housing having an enclosed chamber;

drive means having a first end adapted to be connected to said rotor for rotationally mounting said rotor within said enclosed chamber, said drive means having a second end outside of said enclosed chamber; and vacuum means for evacuating gas from said enclosed chamber via an evacuation port positioned within a volume defined by said axial cavity of said rotor when said rotor is connected to said drive means, said vacuum means including a gas evacuation path having an upstream portion leading to said evacuation port and a downstream portion extending from said evacuation port, said upstream and downstream portions having a generally side-by-side relationship, gas flow through said upstream and downstream portions thereby being in generally opposite directions.

2. The device of claim 1 wherein said drive means includes a hub and a substantially vertical drive shaft, said hub having a downwardly depending skirt surrounding an upper region of said drive shaft, said vacuum means including a sleeve projecting between said drive shaft and said hub, said upstream portion of said gas evacuation path being a space between said sleeve and said skirt of said hub, said downstream portion of said gas evacuation path being a space between said sleeve and said drive shaft.

3. The device of claim 2 wherein said sleeve is an annular member that is coaxial with said drive shaft, said upstream portion of said gas evacuation path being at a radially outward surface of said sleeve, said downstream portion being at a radially inward surface of said sleeve.

4. The device of claim 1 wherein said drive means includes a drive motor, said vacuum means being in fluid communication with said drive motor.

5. The device of claim 1 wherein said vacuum means includes a vacuum pump.

6. A device for centrifugally separating a sample comprising:

a housing having an enclosed chamber, said chamber having a bottom wall;

a drive shaft extending through said bottom wall to said chamber, said drive shaft having an upper end within said chamber;

a conduit adjacent to said drive shaft to provide a gas evacuation path, said conduit having an inlet within said chamber; and a rotor, one of said rotor and said drive shaft having means for releasably connecting said rotor to said drive shaft such that fluid communication from said chamber to said inlet is substantially in an upward direction from said bottom wall.

7. The device of claim 6 wherein said means for connecting said rotor to said drive shaft includes a hub having an inverted, generally U-shaped cross section, said hub being fit onto said drive shaft in spaced relation to said conduit and to said bottom wall, thereby forming a path along said hub to said inlet.

8. The device of claim 7 wherein said path along said hub is a generally vertical path to said inlet.

9. The device of claim 6 wherein said conduit is a cylindrical sleeve extending coaxially with said drive shaft, said gas evacuation path being an annular gap between said drive shaft and said sleeve.

10. The device of claim 9 wherein upper and lower extents of said rotor are on opposite sides of said inlet within said chamber.

11. The device of claim 6 further comprising a vacuum pump in fluid communication with said conduit to evacuate gas from said chamber via said inlet.

12. The device of claim 11 further comprising a drive motor connected to said drive shaft to rotate said drive shaft, said vacuum pump being in fluid communication with said drive motor to exhaust gases therefrom.

13. A centrifuge device comprising:

a housing having a bottom wall and having a cover;

a drive shaft extending through said bottom wall, said drive shaft having a lower end and an upper end;

a drive motor connected to said lower end of said drive shaft;

a sleeve surrounding a lower region of said drive shaft within said housing, said sleeve being spaced apart from said drive shaft to provide a gap, said sleeve having an evacuation port;

vacuum means in fluid communication with said gap for removing gas from said housing via said gap; and a hub connected to said upper end of said drive shaft, said hub having a downwardly depending skirt extending over said evacuation port of said sleeve to limit fluid communication between said evacuation port and said housing to a downward path between said hub and said sleeve.

14. The device of claim 13 wherein said sleeve is an annular member having an inside diameter greater than a diameter of said drive shaft, said downwardly depending skirt of said hub being an annular skirt having an inside diameter greater than an outside diameter of said sleeve.

15. The device of claim 13 wherein said vacuum means is in fluid communication with said drive motor to exhaust air from said drive motor.

16. The device of claim 13 further comprising a seal about said sleeve at penetration of said sleeve through said bottom wall of said housing.

17. The device of claim 13 further comprising a rotor attached to said hub, the distance between said bottom wall and said evacuation port being greater than the distance between said bottom wall and said rotor.

* * * * *